US00PP28053P2

(12) United States Plant Patent
Yates

(10) Patent No.: US PP28,053 P2
(45) Date of Patent: May 23, 2017

(54) ***PENSTEMON* PLANT NAMED 'YAPROSE'**

(50) Latin Name: ***Penstemon* hybrid**
Varietal Denomination: YAPROSE

(71) Applicant: Frederic C. Yates, Congleton (GB)

(72) Inventor: Frederic C. Yates, Congleton (GB)

( * ) Notice: Subject to any disclaimer, the term of this patent is extended or adjusted under 35 U.S.C. 154(b) by 0 days.

(21) Appl. No.: 14/999,097

(22) Filed: Mar. 30, 2016

(51) Int. Cl.
*A01H 5/02* (2006.01)

(52) U.S. Cl.
USPC ..... Plt./465

(58) Field of Classification Search
USPC ..... Plt./465
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Penstemon* plant named 'YAPROSE' that is characterized by its flowers that are rosy red with a white throat, its flowers that are outward facing and presented symmetrically on the flowering stem, its short flowering stems with short internode lengths, its good basal branching resulting in repeat flowering and its seedpods that remain green for a long period and up to frost.

2 Drawing Sheets

Botanical classification: *Penstemon* hybrid.
Cultivar designation: 'YAPROSE'.

CROSS REFERENCE TO RELATED APPLICATIONS

This application is co-pending with U.S. Plant Patent Applications filed for plants derived from the same breeding program that are entitled *Penstemon* Plant Named 'YAPMINE' (U.S. Plant patent application Ser. No. 14/999,098) and *Penstemon* Plant Named 'YAPRUBY' (U.S. Plant patent application Ser. No. 14/999,099).

BACKGROUND OF THE INVENTION

The present invention relates to a new and distinct cultivar of *Penstemon* plant of hybrid origin, botanically known as *Penstemon* 'YAPROSE' and will be referred to hereafter by its cultivar name, 'YAPROSE'. The new cultivar represents a new herbaceous perennial grown for garden and container use.

The new invention arose from an ongoing controlled breeding program conducted by the Inventor in Congleton, Cheshire, United Kingdom with the main objectives of developing new cultivars of *Penstemon* with good basal branching, shorter branch internodes and long blooming periods.

'YAPROSE' was derived from a cross made in mid June of 2012 between unnamed and unpatented proprietary plants of *Penstemon* of hybrid origin from the Inventor's breeding program as both the female parent and male parent. 'YAPROSE' was selected in August of 2013 as a single unique plant from amongst the resulting seedlings.

Asexual propagation of the new cultivar was first accomplished by the Inventor by stem cuttings in 2013 in Congleton, Cheshire, United Kingdom. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'YAPROSE' as a unique cultivar of *Penstemon*.

1. 'YAPROSE' exhibits flowers that are rosy red with a white throat.
2. 'YAPROSE' exhibits flowers that are outward facing and presented symmetrically on the flowering stem.
3. 'YAPROSE' exhibits short flowering stems with short internode lengths.
4. 'YAPROSE' exhibits good basal branching resulting in repeat flowering.
5. 'YAPROSE' exhibits seedpods that remain green for a long period and up to frost.

The female parent of 'YAPROSE' differs from 'YAPROSE' in having flowers that are held more downward and that are less symmetrical on the flowering stem. The male parent of 'YAPROSE' differs from 'YAPROSE' in having a less compact plant habit. 'YAPROSE' can most closely be compared to its sibling cultivars 'YAPMINE' and 'YAPRUBY'. Both are similar to 'YAPROSE' in growth and flowering characteristics other than flower color. 'YAPMINE' differs from 'YAPROSE' in having flowers that are more purple in color with a white throat. 'YAPRUBY' differs from 'YAPROSE' in having flowers that are more red in color with a white throat.

BRIEF DESCRIPTION OF THE DRAWINGS

The accompanying colored photographs illustrate the overall appearance and distinct characteristics of the new *Penstemon*. The photographs were taken of a 4 month-old plant of 'YAPROSE' as grown in a 2-liter container in Gensingen, Germany.

The photograph in FIG. 1 provides a side view of a plant of 'YAPROSE' in bloom.

Figure 1:
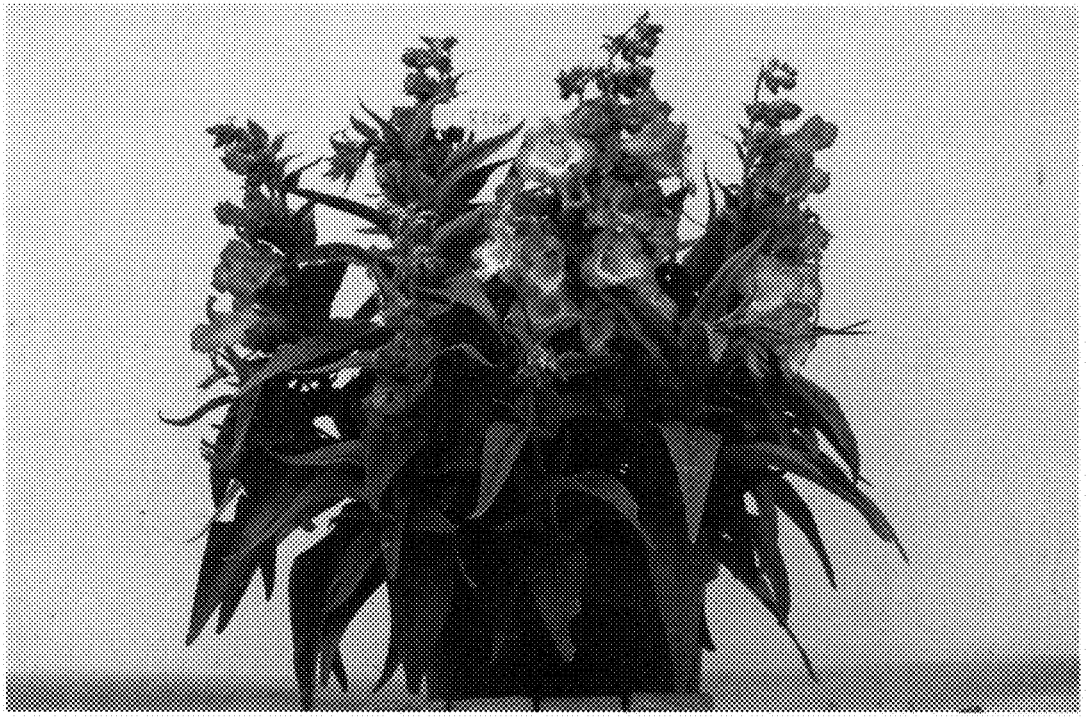
Figure 2:
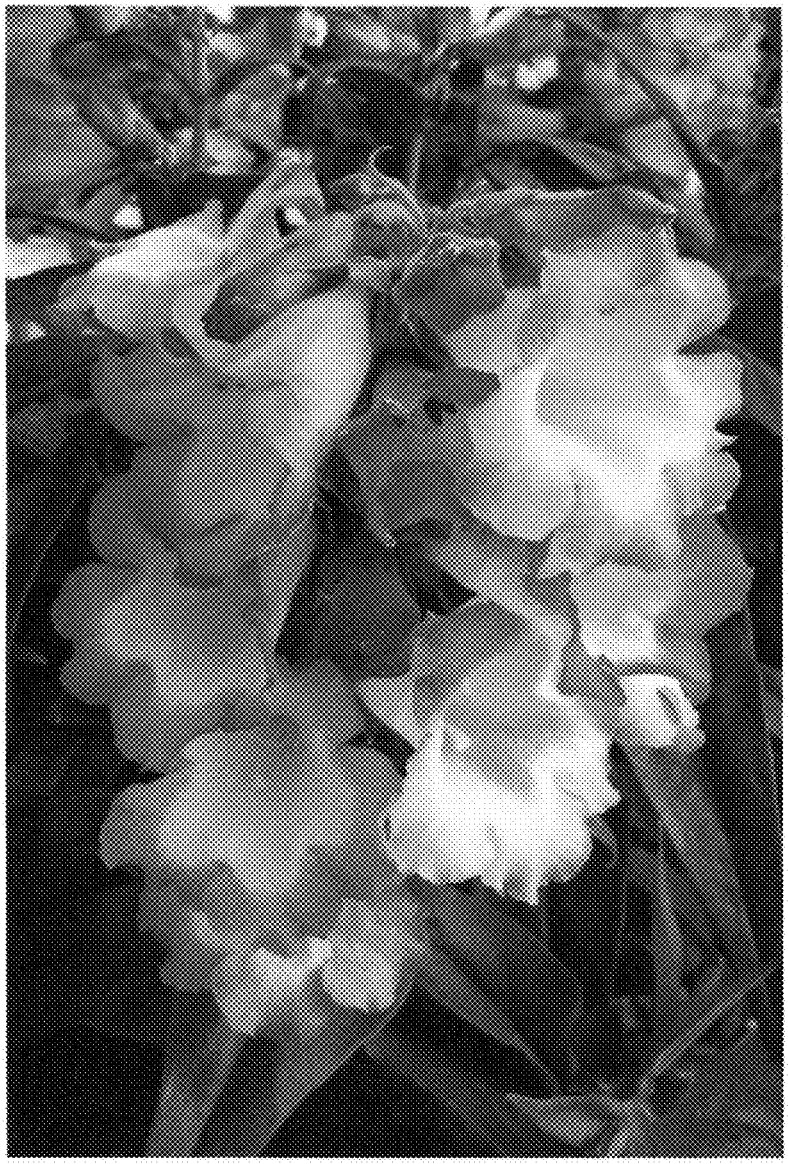

The photograph in FIG. 2 provides a close-up view of the inflorescences of 'YAPROSE'.

The colors in the photographs are as close as possible with the photographic and printing technology utilized and the color values cited in the Detailed Botanical Description accurately describe the colors of the new *Penstemon*.

DETAILED BOTANICAL DESCRIPTION OF THE PLANT

The following is a detailed description of 6 month-old plants of the new cultivar as grown outdoors in 25-cm containers in Hampshire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late May through October in The United Kingdom.

*Plant type*.—Herbaceous perennial.

*Plant habit*.—Upright with compact flowering stems.

*Height and spread*.—An average of 30 cm in height and 38 cm in spread.

*Hardiness*.—At least in U.S.D.A. Zone 5.

*Diseases and pests*.—No susceptibility or resistance to diseases or pests has been observed.

*Root description*.—Fine, fibrous, NN155B in color.

Growth and propagation:

*Propagation*.—Stem cuttings.

*Time required for root development*.—An average of two weeks for root initiation about six weeks to produce a young rooted plant.

*Growth rate*.—Moderate.

Stem description:

*Branch habit*.—Continuously produced basal stems throughout the growing season.

*Stem size*.—An average of 30 cm (including peduncle) in length and 4 mm in diameter.

*Stem shape*.—Rounded.

*Stem color*.—144C.

*Stem surface*.—Glabrous but pubescent at apex with short translucent simple hairs.

*Stem aspect*.—Held at an average angle of 45°.

*Stem strength*.—Strong.

*Internode length*.—1 to 2.5 cm (at center of stem).

Foliage description:

*Leaf shape*.—Lanceolate.

*Leaf division*.—Simple.

*Leaf size*.—An average of 10 cm in length and 2.5 cm in width.

*Leaf quantity*.—About 22 (11 pairs) per stem.

*Leaf base*.—Rounded.

*Leaf apex*.—Acuminate.

*Leaf fragrance*.—None.

*Leaf color*.—Upper surface; a color between 137C and 146B, lower surface 138B.

*Leaf venation*.—Pinnate pattern, only mid rib is conspicuous, color 144D on both surfaces.

*Leaf margins*.—Shallowly serrate.

*Leaf attachment*.—Sessile and clasping.

*Leaf arrangement*.—Opposite.

*Leaf surface texture*.—Glabrous on upper and lower surface.

Flower description:

*Inflorescence type*.—Terminal cyme.

*Inflorescence size*.—An average of 20 cm in length and 8 cm in width.

*Lastingness of inflorescence*.—About 10 days, self-cleaning.

*Flower size*.—An average of 3.2 cm in depth and 3.9 cm in diameter.

*Flower fragrance*.—None.

*Flower number per inflorescence*.—An average of 25 flowers.

*Flower shape*.—Broadly tubular.

*Flower aspect*.—Horizontal.

*Flower buds*.—Ovoid in shape, an average of 3 cm in length and 1.1 cm in width, 150C, apex 47B in color, surface is glabrous.

*Flower petals*.—5, fused into tube with lobes free, lobes; rounded in shape, margins entire and slightly wavy, obtuse apex, an average of 3 cm in length and 1.5 cm in width, slightly recurved, inside surface texture smooth, outside surface covered with translucent pubescent hairs, both surface colors; 55B, becoming 61D at the margins, tube; average of 1.4 cm in length and 1.8 cm in width, inner surface color 155A, outer surface color 155A, with markings of 63B to 63C, on sun exposed side color fades to 155A at the base.

*Bracts*.—2 per flower, ovate to narrow ovate in shape, acuminate apex, rounded base, short translucent pubescence covers both surfaces, an average of 1.7 cm in length and 7 mm in width, 143C in color on both surfaces.

*Sepals*.—An average of 5, rotate, ovate in shape, entire margin, acute apex, fused at base, an average of 7 mm in length and 5 mm in width, upper and lower surfaces are 144C in color.

*Calyx*.—Rotate.

*Peduncle*.—Same characteristics as stem description, inflorescence portion an average of 20 cm in length.

*Pedicel*.—Rounded in shape, an average of 6 mm in length and 1 mm in diameter, moderately strong in strength, 144C in color, glabrous and smooth surface texture.

Reproductive organs:

*Gynoecium*.—1 Pistil, style; an average of 2 cm in length and 1 mm in width, 71D in color; stigma; club-shaped, 2 mm in length and 1 mm in width, NN155A in color, ovary; narrow conical in shape, superior, 5 mm in length and 3 mm in width, glabrous surface, 144C in color.

*Androecium*.—4 stamens, (2 longer and 2 shorter), filament; 1.5 to 1.8 cm in length, 1 mm in width and 155B in color, anther; an average of 3 mm in length and 1 mm in width, N186B to N186C in color, pollen is moderate in quantity and NN155A in color.

*Fruit and seed*.—Capsule; remains green (144A) throughout growing season, seeds; few per capsule, ellipsoid in shape, N199 in color, and 1.5 mm in length and >1 mm in width.

It is claimed:

1. A new and distinct cultivar of *Penstemon* plant named 'YAPROSE' as herein illustrated and described.

* * * * *